United States Patent [19]
Neely

[11] Patent Number: 6,159,701
[45] Date of Patent: *Dec. 12, 2000

[54] METHOD AND COMPOSITIONS FOR TREATING AND DIAGNOSING TUMORS USING ADENOSINE RECEPTOR ACTIVATED CELLS

[75] Inventor: Constance Neely, Raleigh, N.C.

[73] Assignee: Link Technology Incorporated, Raleigh, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/748,559

[22] Filed: Nov. 8, 1996

[51] Int. Cl.$^7$ .................................................. G01H 33/53
[52] U.S. Cl. ...................... 435/7.23; 435/7.1; 435/372; 530/300; 530/350
[58] Field of Search .......................... 435/372, 7.1, 7.23; 530/300, 350

[56] References Cited

U.S. PATENT DOCUMENTS

| | | | |
|---|---|---|---|
| 4,880,918 | 11/1989 | Rapaport | 514/46 |
| 4,904,472 | 2/1990 | Belardinelli et al. | 514/263 |
| 4,980,379 | 12/1990 | Belardinelii et al. | 514/263 |
| 5,049,372 | 9/1991 | Rapaport | 424/1.77 |
| 5,200,176 | 4/1993 | Wong et al. | 424/85.1 |

OTHER PUBLICATIONS

Hamilton, TA. et al. 1987. Immunol. Today 8:151–158, 1987.
Salmon, JE et al. 1993. J. Immunol. 151(5):2775–2785, 1993.
BbaHacharya S. et al. 1995. BBA 1265:15–21, 1995.
Gerwin, P. et al. 1991. Mol. Pharmacol. 40:149–55, 1991.
Arya, G. et al. 1995. J. Surgical Res. 59:13–16, 1995.
Bowling, WM. et al. 1996. J. Surgical Res. 63:287–292, 1996.
Patel, A et al. 1988. Mol. Pharmacol. 33:585–591, 1988.
R.R. Aksamit et al; Inhibition of Chemotaxis by S–3–Deazaadenosylhomocysteine in a Mouse Macrophage Cell Line; *The Journal of Biological Chemistry* 257 No. 2, pp. 621–625 (1982).
P. Alexander and R. Evans; Endotoxin an dDouble Stranded RNA render Macrophages Cytotoxic; *Nature New Biology* 232, pp. 76–78 (1971).
S. Apasov et al; Role of Extracellular ATP and P1 and P2 Classes of Purinergic Receptors in T–cell Development and Cytotoxic T Lymphocyte Effector Functions; *Immunological Reviews* 146, pp. 5–19 (1995).
C.D. Beaty et al; Lipopolysaccharide–induced cytokine production in human monocytes: role of tyrosine phosphorylation in transmembrane signal transduction; *Eur. J. Immunol.* 24, pp. 1278–1284 (1994).
T.Y. Chen et al; Lipopolysaccharide Receptors and Signal Transduction Pathways in Mononuclear Phagocytes; *Current Topics in Microbiology and Immunology* 181 pp. 169–188 (1992).

S. D'Ancona et al; The Effect of Dilazep on F10 Cells in Vitro; *Anticancer Research* 12 pp. 631–635 (1992).
S. D'Ancona et al; Effect of Dipyridamole, 5'–(N–Ethyl)–carboxamidoadenosine and 1,3–Dipropyl–8–(2–amino–4–chlorophenyl)–xanthine on LOVO Cell Growth and Morphology; *Anticancer Research* 14, pp. 93–98 (1994).
A.Y. Divekar et al; Changes in Sarcoma 180 Cells Associated with Drug–induced Resistance to Adenosine Analogs$^1$; *Cancer Research* 32, pp. 2530–2537 (Nov. 1972).
M. D. Sauro et al; Adenosine Activation of a Nuclear Pool of Protein Kinase C in Rat Splenocytes; *Life Sciences* 46, pp. 1293–1300 (1990).
B.A. Eppell et al; Adenosine Receptors are expressed during differentiation of monocytes to macrophages in vitro; *The Journal of Immunology* 143 No. 12; pp. 4141–4145 (1989).
W–G Fang et al; $P_2$–Purinergic Receptor Agonists Inhibit the Growth of Androgen–Independent Prostate Carcinoma Cells; *The Journal of Clinical Investigation, Inc.* 89, pp. 191–196 (1992).
L.M. Flebbe et al; Activation of C3H/HeJ Macrophage Tumoricidal Activity and Cytokine Release by R–Chemotype Lipopolysaccharide Preparations; *The Journal of Immunology* 145 No. 5; pp. 1505–1511 (1990).
K.B. Glaser et al; Bacterial Lipopolysaccharide Priming of $P388D_1$ Macrophage–like Cells for Enhanced Arachidonic Acid Metabolism; *The Journal of Biological Chemistry*; 265, No. 15; pp. 8658–8664 (1990).
J.T. Grace et al; $N^6$–Substituted Adenine Derivatives as Growth Inhibitors of Human leukemic Myeloblasts and S–180 Cells; *Abstracts* Mar. 1967.
D. Lappin & K. Whaley; Adenosine A2 receptors on human monocytes modulate C2 production; *Clin. exp. Immunol.* 57, pp. 454–460 (1984).
H.A. Leaver et al; Phagocyte responses to endotoxin: intracellular signals and oxidative activity; *FEMS Microbiology Immunology* 47 pp. 293–294 (1989).
H. Loppnow et al; Induction of Cytokines in Mononuclear and Vascular Cells by Endotoxin and Other Bacterial Products; *Methods in Enzymology* 236, pp. 3–10 (1994).
M.R. Marvin et al; A Novel Tumor–Derived Mediator that Sensitizes Cytokine–Resistant Tumors to Tumor Necrosis Factor; *Journal of Surgical Research* 63, pp. 248–255 (1996).

(List continued on next page.)

*Primary Examiner*—Paula K. Hutzell
*Assistant Examiner*—Minh-Tam Davis
*Attorney, Agent, or Firm*—Myers Bigel Sibley & Sajovec

[57] ABSTRACT

Methods of treating and/or imaging tumors utilize $A_1$ adenosine-receptor activated cells (such as monocytes and macrophages) are described. Activated cells may be administered systemically or locally, and may be radiolabelled to provide imaging and diagnostic functions. Macrophages resident in tissues may be primed and activated for use in treating and imaging tumors.

12 Claims, No Drawings

OTHER PUBLICATIONS

J.E. McCormick and R. Stanley McElhinney; Nucleoside Analogues, Part $2^1$ Further Molecular Combinations of (5–Substituted) Uracil and N–(2–Chloroethyl)–N–nitrosoursea Residues as Anticancer Agents; *Chem. Soc. Perkin Trans* pp. 93–100 (1985).

C.F. Neely and I.M. Keith; $A_1$ adenosine receptor antagonists block ischemia–reperfusion injury of the lung; *The American Physiological Society* pp. 1036–1046 (1995).

C.F. Neely et al; Purinergic Responses in the Feline Pulmonary Vascular Bed; *Drug Development Research* 28 pp. 328–335 (1993).

C.F. Neely et al; Adenosine and ATP Produce Vasoconstriction in the Feline Pulmonary Vascular Bed by Different Mechanisms$_1$; *The Journal of Pharmacology and Experimental Therapeutics*; 258 No. 3; pp. 753–760 (1991).

C.F. Neely and I. Matot; Pharmacological probes for $A_1$ and $A_2$ adenosine receptors in vivo in feline pulmonary vascular bed; *The American Physiological Sciety* pp. H610–619 (1996).

S. Ogawa et al; Hypoxia–induced increased permeability of endothelial monolayers occurs through lowering of cellular cAMP levels; *American Physiological Society* pp. C546–C554 (1992).

U. Prabhakar et al; Inhibition of LPS–induced TNFα production in human monocytes by adenosine ($A_2$) receptor selective agonists; *Int. J. Immunopharmae* 17 No. 3, pp. 221–224 (1995).

T. Priebe et al; Adenosine Receptors and Modulation of Natural Killer Cell Activity by Purine Nucleosides$_1$; *Cancer Research* 50, pp. 4328–4331 (Jul. 1990).

E. Ragazzi et al; Dipyridamole as a modulator of multidrug resistance in tumour cells in vitro; *International Journal of Oncology* 6; pp. 659–662 (1995).

J.A. Rankin et al; Macrophages Cultured in Vitro Release Leukotriene $B_4$ and Neutrophil Attractant/Activation Protein (Interleukin 8) Sequentially in Response to Stimulation with Lipopolysaccharide and Zymosan; *The Journal of Clinical Investigation, Inc.* 86, pp. 1556–1564 (1990).

F.G. Sajjadi et al; Inhibition of TNF–α Expression by Adenosine; *The American Association of Immunologists* pp. 3435–3442 (1996).

W.L. Salzer and C.E. McCall; Primed Stimulation of Isolated Perfused Rabbit Lung by Endotoxin and Platelet Activating Factor Induces Enhanced Production of Thromboxane and Lung Injury; *Endotoxin–primed Lung Injury* pp. 1135–1143 (1990).

K. Sato et al; Tolerance to the Anti–Metastatic Effect of Lipopolysaccharide Against Liver Metastasis in Mice; *Int. J. Cancer* 66, pp. 98–103 (1996).

A.G. Stewart and T. Harris; Adenosine inhibits platelet–activating factor, but not tumour necrosis factor–α–induced priming of human neutrophils; *Immunology* 78, pp. 152–158 (1993).

D. Suk et al; *Toxicological and Antiproliferative Effects of $N^6$–($\Delta^2$–Isopentenyl) adenosine, a Natural Component of Mammalian Transfer $RNA_1$*; Cancer Research 30, pp. 1429–1436 (May 1970).

H.B. Tey et al; Adenosine Modulates Cell Growth in Human Epidermoid Carcinoma; *Biochemical and Biophysical Research Communications* 187, No. 3 pp. 1486–1492; (1992).

R.Thedford et al; Cytotoxicity of $N^6$–Cycloalkylated Adenine and Adenosine Analogs to Mouse Hepatoma Cells; 57, pp. 53–59 (1989).

R.W. Trewyn and S.J. Kerr; Cytotoxicity of $N^6$–Substituted Adenosine Analogs to Cultured Trophoblastic Tumor Cells; *Biochemical Pharmacology* 28 pp. 607–612 (1979).

Z.Yang et al; Signal Transduction Pathways of Bacterial Lipopolysaccharide–Stimulated Bovine Vascular Endothelial Cells; *Inflammation* 18 No. 2; pp. 221–233 (1994).

Neely et al., $A_1$ Adenosine Receptor Antagonists Block Ischemia–Reperfusion Injury of the Lung, *American Journal Of Physiology*, (Jun. 1995), vol. 268 (6 Pt 1) pp. L1036–L1046

Bowlin et al., Adeosine $A_3$ Receptor Agonsits Inhibit Murine Macrophase Tumor Necrosis Factor α Production in Vitro and in Vivo, *Cellular and Molecular Biology*, May 1997, vol. 43, No. 3, 99. 345–349.

Liles et al.,Activation of Protein Kinase C Induces Rapid Internationalization and Subsequent Degradation of Muscarinic Acetylcholine Receptors in Neuroblastoma Cells, *J. Biological Chemistry*, Apr. 25, 1986, vol. 261, No. 12 pp. 5307–5313.

Bauldry et al., Tumor Necrosis factor–α Priming of Phospholipase $A_2$ Activation in Human Neutrophils: An Alternative Mechanism of Priming J. Immunology (Feb. 15, 1991) vol. 146, pp. 1277–1285.

METHOD AND COMPOSITIONS FOR TREATING AND DIAGNOSING TUMORS USING ADENOSINE RECEPTOR ACTIVATED CELLS

FIELD OF THE INVENTION

The present invention relates to methods of treating and or imaging tumors, and particularly to methods of treating and/or imaging tumors using $A_1$ adenosine-receptor activated cells, such as monocytes, macrophages and/or splenocytes.

BACKGROUND OF THE INVENTION

Purinergic receptors can be classified into the $P_1$ (adenosine) receptors and the $P_2$ (adenosine 5' triphosphate) receptors. Adenosine receptors can further be delineated into major subclasses, the $A_1$, $A_2$ ($A_{a2}$ and $A_{a2b}$) and $A_3$ adenosine receptors. These subtypes are differentiated by molecular structure, radioligand binding profiles, and by pharmacological and functional activity. Binding of adenosine, a naturally occurring nucleoside, to specific adenosine receptors leads to either stimulation ($A_2$-receptor activation) or inhibition ($A_1$-receptor activation) of adenylate cyclase activity resulting in an increase or decrease of intracellular cAMP, respectively. Most tissues and cell types possess either the $A_1$ or $A_2$ receptor, or both. Moreover, $A_1$ adenosine receptors have been identified in the nuclear fraction of splenocytes (Donnabella, Life Sci. 46:1293 (1990)). Specific $A_1$, $A_2$, and $A_3$ antagonists and agonists are well-known in the art. See, e.g., Trivedi et al., Structure-Activity Relationships of Adenosine $A_1$ and $A_2$ Receptors, In: Adenosine and Adenosine Receptors, M. Williams, Ed., Humana Press, Clifton, N.J., USA (1990); Jacobson et al., J. Medicinal Chem. 35:407 (1992); Fredholm et al., Pharm. Rev. 46:143 (1994); Jacobson, Abstracts from Purines '96, Drug Dev. Res., March 1996, page 112. Divalent ions ($Mg^{2+}$ and $Ca^{2+}$) and allosteric enhancers enhance the binding of $A_1$ adenosine receptor agonists to $A_1$ adenosine receptors (Kollias-Baker, Circ. Res. 75:961 (1994)). Allosteric enhancers enhance $A_1$ receptor mediated responses and are described in Bhattacharya, Biochim. Biophys. Acta 1265:15 (1995).

Inflammatory cells, including monocytes and alveolar macrophages are known to express the $A_1$, $A_2$ and $A_3$ receptor subtypes. Eppell et al., J. Immunology 143:4141 (1989); Lapin and Whaley, Clin. Exp. Immunol. 57:454 (1984); Saijadi, et al., J. Immunol. 156:3435 (1996). Activation of the $A_3$ or $A_2$ receptors has been shown to inhibit monocyte function.

Mature monocytes enter the circulatory system from the bone marrow; some monocytes enter tissues and develop into macrophages in the spleen, lymph nodes, liver, lung, thymus, peritoneum, nervous system, skin and other tissues. Monocytes and macrophages can be identified by morphology, cell surface antigens, and the presence of characteristic enzymes. Both monocytes and macrophages play a role in inflammatory responses by eliminating bacteria and other pathogens by phagocytosis. Monocytes and macrophages also secrete various proteins active in immune and inflammatory responses, including Tumor Necrosis Factor (TNF) and Interleukin I (IL-1)). Upon stimulation, monocytes and macrophages can generate various oxygen metabolites, including superoxide anion and $H_2O_2$ that are toxic to both pathogens and normal cells.

SUMMARY OF THE INVENTION

A first aspect of the present invention is a method of inhibiting the growth of tumor cells in a subject, wherein a sample of treatment cells is taken from a subject and contacted with a priming agent, and then activated by contact with an $A_1$ adenosine receptor agonist, in order to induce cytotoxicity in the treatment cells. The cytotoxic treatment cells are then administered to the subject.

A further aspect of the present invention is a method of inhibiting the growth of tumor cells in a subject, wherein a macrophage priming agent is administered to tissue containing tumor cells, in an amount sufficient to prime resident macrophages. An $A_1$ adenosine receptor agonist is then administered to the tissue containing the tumor cells to induce cytotoxicity in the primed macrophages.

A further aspect of the present invention is a method of imaging tumor cells in vivo in a subject, wherein a sample of treatment cells is taken from a subject and contacted with a priming agent, and then labeled with a radiolabelled selective $A_1$ adenosine receptor ligand. The radiolabelled, primed treatment cells are then administered to the subject to provide a radioimage of any tumor cells present.

Fang et al. reported the inhibition of cell growth in hormone-refractory prostate cancer cell lines using $P_2$ purinergic receptor agonists. These authors concluded that human androgen-independent prostate carcinoma cells expressed functional $P_2$-purinergic receptors, and proposed that agonists of such receptors be used to inhibit the growth of related neoplasms. Methods of treating prostate cancers by administration of a $P_2$ purinergic receptor agonist are provided in U.S. Pat. No. 5,415,873.

U.S. Pat. No. 4,880,918 (Rapaport) reports the use of low doses of extracellular adenosine 5'-diphosphate (ADP) or adenosine 5'-triphosphate (ATP) for the selective inhibition of growth and subsequent cell death of malignant cells. Such treatment is reported as inhibiting malignant cell growth without affecting normal cell activity. ATP and ADP are stated as able to permeate the plasma membrane of tumor cells (but not normal animal cells) without prior degradation to adenosine 5'-monophosphate (AMP) or adenosine. It is stated that the effects of ADP and ATP cannot be duplicated with the use of AMP or adenosine.

U.S. Pat. No. 5,049,372 (Rapaport) reports that administration of adenine nucleotides (AMP, ADP or ATP) into a host results in elevation of extracellular blood plasma ATP levels, which in turn inhibit tumor growth as well as ameliorating cancer cachexia in tumor-bearing hosts.

Tey et al. Biochem. Biophys. Res. Comm. 187:1486 (1992) report that adenosine evoked a biphasic response in cultured human epidermoid carcinoma cells. A low concentration inhibited colony formation while higher concentrations progressively reversed the inhibition. When both $A_1$ and $A_2$ receptors were blocked, however, colony formation or growth was not inhibited at low concentrations of adenosine but was inhibited at high concentrations.

D'Ancona et al. reported the in vitro effects of NECA (5'-(N-ethyl) -carboxamidoadenosine), an $A_1$ and $A_2$ adenosine receptor agonist, and 1,3-dipropyl-8-(2-amino-4-chloropheny)-xanthine (PACPX), a selective $A_1$ adenosine receptor antagonist, administered directly to human metastatic cell lines. Anticancer Research 14:93 (1994). The drugs were reported as having an inhibitory effect on cell growth.

The foregoing and other objects and aspects of the present invention are explained in detail in the specification set forth below.

DETAILED DESCRIPTION OF THE INVENTION

A direct interaction of macrophages and tumor cells, in an approximately 20:1 ratio (macrophages:tumor cells), has been reported as required for the tumoricidal effect of macrophages to be seen. Alexander and Evans, *Nature New Biology* 232:76 (1971). It is not fully understood how the actual cytotoxic effects of macrophages on tumor cells occurs.

Relatively low concentrations of bacterially derived endotoxic lipopolysaccharides (LPS) are known to activate macrophages, stimulating the macrophages to synthesize and secrete immunologically important cytokines, including interferon-α/β, interleukin-1, and tumor necrosis factor. See Alexander, *Nature New Biology* 232:76–78 (1971); Pace and Russell, *J. Immunol.* 126:1863 (1981); Hamilton and Adams, *Immunology Today* 8:151 (1987); Chen et al., *Curr. Topics Microbiol. Immunol.* 181:169 (1992). Exposure to LPS can result in fully activated macrophages capable of killing tumor cells. Saturable and specific binding of LPS to peritoneal macrophages has been reported. Haeffner-Cavaillon et al., *J. Immunol.* 128:1950 (1982). However, the biochemical sequence of events triggered by LPS interaction with macrophages which results in the tumoricidal activation of macrophages has not yet been defined. It has been suggested that LPS activation of the $G_i$ protein may be involved in macrophage interactions. See Chen et al., *Curr. Topics Microbiol. Immunol.* 181:169 (1992).

The presence of $A_2$ receptors on monocytes has been reported. Lappin and Whaley, *Clin. Exp. Immunol.* 57:454 (1984). The presence of $A_1$, $A_2$, and $A_3$ adenosine receptors has been reported on human differentiated macrophages primed with phorbol myristoyl acetate (PMA) (Saijadi et al., *J. Immunol.* 156:3435 (1996)). Activation of $A_2$ or $A_3$ adenosine receptors has been reported to inhibit the release of tumor necrosis factor from activated (LPS induced) human monocytes (macrophages). Prabhakar, *International J. Immunopharm.* 17:221 (1995); Saijadi et al., *J. Immunol.* 156:3435 (1996). Activation of $A_2$ adenosine receptors is also known to stimulate cell proliferation (in chick brain astrocytes). Rathbone, *Medical Hypothesis* 37:213 (1992).

Macrophages, when stimulated by any of a variety of ligands or compounds, undergo a cyanideinsensitive respiratory burst and concomitantly secrete reactive oxygen intermediates. Oxygen consumption is greatly increased during this respiratory burst. Products released by macrophages during such metabolic bursts may be used as markers in the analysis of signal transduction mechanisms which lead to rapid macrophage responses. See Hamilton and Adams, *Immunology Today* 8:151 (1987).

These metabolic bursts of macrophages can be enhanced, or primed, by exposure to stimuli which do not, in themselves, trigger a metabolic burst. See Babior, *Blood* 64:959 (1984); Babior *J. Clin. Invest.* 73:599 (1984). Phorbol myristoyl acetate (PMA, a stimulant of protein kinase C (PKC)) is known to prime macrophages for activation. Hamilton and Adams, *Immunology Today* 8:151 (1987). Thus, macrophages may first be primed (for example by exposure to PMA or IFNα) and then interact with LPS to become fully activated. As used herein, "activated" macrophages are those which possess tumoricidal functions. As used herein, "priming" of macrophages refers to a treatment which enhances the metabolic burst of macrophages, wherein the metabolic burst is increased over that which would occur in the absence of priming. As used herein, "primed" macrophages refers to those that have undergone a priming treatment; "primers" or "priming agents" refer to agents capable of priming macrophages.

Thus the induction of tumoricidal effects in cells such as and including macrophages may occur in two steps, including a first response to a priming factor and a second response to a an activating factor (such as LPS) which induces tumoricidal effects. Exposure to the first priming factor lowers the dose requirement for the activating factor.

Following ischemia and reperfusion, activation of $A_1$ adenosine receptors present on pulmonary arterial endothelial cells results in a cytotoxic effect. In heart tissue adenosine, $A_1$ adenosine receptor agonists, or a brief period (from approximately 5 to about 15 minutes) of preconditioning ischemia attenuates ischemiareperfusion (I-R) injury. See, e.g. Neely and Keith, *Am. J. Physiol.* 268:L1036 (1995). In the lung, thromboxane is released during ischemia and is a mediator of I-R injury. Adenosine produces vasoconstriction in the pulmonary vascular bed by acting on $A_1$ receptors to induce the release of thromboxane. These vasoconstrictor responses in endothelial cells are desensitized by prior treatment with low doses of $A_1$ receptor agonists. It was hypothesized that during preconditioning ischemia, adenosine attenuates ischemia-reperfusion injury of the heart by activation and subsequent desensitization of $A_1$ adenosine receptors. Preconditioning ischemia attenuates ischemia-reperfusion (I-R) injury of both lung and heart. In view of these findings, Neely and Keith (1995) hypothesized that during longer periods of ischemia (longer than about 10 to about 15 minutes), greater amounts of adenosine are released, which activates $A_1$ receptors; thus if an initial desensitization of $A_1$ receptors is the mechanism by which preconditioning ischemia attenuates I-R injury, and $A_1$ receptor activation during prolonged periods of ischemia initiates I-R injury of the lung and heart, $A_1$ receptor antagonists should provide a protective effect in I-R injury of the lung and heart. $A_1$ receptor antagonists were in fact found to protect against I-R injury in vivo in the lung and heart in animal models (Neely and Keith, *Am. J. Physiol., Lung Cell. Mol. Physiol.* 268:L1036 (1995); Neely et al., *Circulation* November 1996). Additionally, the present inventor has found that following hypoxia/anoxia of pulmonary artery endothelial cells, DPCPX (a highly selective $A_1$ adenosine receptor antagonist) inhibits an increase in an enzyme (phospholipase $A_2$ ($PLA_2$)) which is important for the release of cytotoxic substances including thromboxane from these cells in vitro; $A_1$ receptor antagonists provide protection against this cytotoxic effect. See U.S. Pat. No. 5,504,090 (Apr. 2, 1996). All patents cited herein are incorporated herein in their entirety.

It is known that lipopolysaccharide (LPS, endotoxin) binds to cells and induces the release of mediators from neutrophils, monocytes, macrophages, and endothelial cells. These mediators are important in the pathophysiology of endotoxin-induced acute lung injury. The present inventor has recently found that, in pulmonary arterial endothelial cells, both $A_1$ adenosine receptor agonists and endotoxin (LPS) induce thromboxane release, that endotoxin induced inhibition of adenylate cyclase or thromboxane release is blocked by a highly selective $A_1$ adenosine receptor antagonist (1,3 dipropyl 8 cyclopentylxanthine (DPCPX)), and that endotoxin displaces the binding of highly selective $A_1$ adenosine receptor antagonist radioligands [$^3$H] DPCPX and $^{125}$I-BW A844U. These findings indicate that LPS binds to and activates $A_1$ adenosine receptors on pulmonary artery endothelial cells. Also, $A_1$ adenosine receptor antagonists are able to block such endotoxin-induced lung injury, supporting that activation of $A_1$ adenosine receptors is important in endotoxin-induced acute lung injury. Neely, Jin and Keith, *Am J. Physiol., Lung Cell Mol. Physiol.*, 268:L1036, 1995.

As described above, evidence indicates that binding of LPS to endothelial cells occurs through $A_1$ adenosine receptors. LPS is known to activate macrophages to become tumoricidal; the present methods utilize $A_1$ adenosine receptor agonists to activate treatment cells (including but not limited to macrophages, monocytes and/or splenocytes) and induce tumoricidal effects in or by such treatment cells similar to those induced by LPS (for example, in macrophages). (As used herein, "treatment cells" refers to the activated cells used to treat or image tumors, to distinguish from the neoplastic cells being treated). The activated, tumoricidal cells release cytotoxic substances, such as tumor necrosis factor. Prior to activation, cells may be primed to increase the tumoricidal effects.

As used herein, the induction of tumoricidal or cytotoxic effects "in" treatment cells, or "by" treatment cells, refers to the induction of cellular activities in treatment cells which allow the treatment cells to have cytotoxic effects on neoplastic target cells. The induction of such effects can be assessed by analyzing the cellular components of the treatment cell, or the factors produced by the treatment cell, or by studying the cytotoxic effects of the treatment cell on an appropriate target cell.

The methods of the present invention also utilize hypoxia and reoxygenation conditions to increase $A_1$ adenosine receptor activation and signal transduction pathways which, following activation, result in the release of cytotoxic substances. As noted above, following ischemia and reperfusion, activation of $A_1$ adenosine receptors present on pulmonary arterial endothelial cells causes a cytotoxic effect (Neely and Keith (1995)), and the release of a cytotoxic substance, thromboxane, has been found by the present inventor to be blocked by an $A_1$ adenosine receptor antagonist (DPCPX). In heart tissue adenosine, $A_1$ adenosine receptor agonists, or a brief period of preconditioning ischemia attenuates ischemia-reperfusion (I-R) injury. In the lung, thromboxane is released during ischemia and is a mediator of I-R injury. Moreover, ischemia and reperfusion enhance the capacity of LPS to produce cytotoxicity and damage organs. Ischemia and reperfusion sensitizes organs to the injurious effects of LPS.

Prior to activation of the treatment cells using the methods provided herein, the number of available $A_1$ adenosine receptors on the cell may be increased by treatment with dexamethasone (Gerwins et al., *Mol. Pharmacol.* 40:149–155 (1991)) or lipofection with plasmids containing cDNA encoding $A_1$ adenosine receptors (Robeva et al., Biochem. Pharmacol. 51:545–555 (1996); Felgner, *Proc. Natl. Acad. Sci.* 84:7413 (1987)). Prior to activation, treatment of cells with an allosteric enhancer (for example, 2-amino-3-benzoylthiophenes such as PD 81,723) increases $A_1$ adenosine receptor ligand binding and stabilizes $A_1$ adenosine receptor-G protein complexes (Bhattacharya, *Biochimica. Biophysica.* 1265:15–21 (1995)).

An undesirable tolerance to $A_1$ adenosine receptor agonists in lung macrophages and other cells having multiple exposures to LPS may occur (Neely, *Am. J. Physiol.* 270 (Heart Circ. Physiol. 39)H610 (1996)). Prior to or concurrent with activation, provision of protein kinase inhibitors to treatment cells prevents tolerance to the tumoricidal effect of LPS (Sato, *Int. J. Cancer* 66:98–103 (1996); Bowling, *J. Surg. Res.* 63:287–292 (1996); Kravchenko et al., *Shock* 5:194–201 (1996)). Also, LPS induces the release of tumor necrosis factor alpha (TNFα) by inducing the phosphorylation of tyrosine and an increase in tyrosine kinases. Tyrosine phosphatase inhibitors such as sodium orthovanadate (vanadate) enhanced LPS induced production of TNFα in monocytes. Beatty, *Eur. J. Immunol.* 24:1278 (1994).

When activating treatment cells in culture, adenosine deaminase (an enzyme responsible for the metabolizing of adenosine) may be added to the culture to decrease or remove free adenosine which may be present in the culture; such adenosine would compete with the adenosine receptor agonist added to the culture to activate the treatment cells.

The methods of the present invention utilize the cytotoxic effects of activated cells (including but not limited to macrophages, monocytes and/or splenocytes) to inhibit the growth of tumor cells. The present methods may be carried out by direct activation of cells by: (1) administering $A_1$ adenosine receptor agonists to cells at the site of the tumor to be treated, (2) isolating and activating cells in vitro with subsequent systemic administration of activated cells to the subject or administration directly to the tumor site, (3) isolating monocytes from the subject to be treated and culturing the monocytes to produce macrophages, which are activated in vitro and then administered systemically to the subject or directly to the treatment site or (4) activating cells obtained from a cell line or other source.

Cells used in the present methods are activated by exposure to any suitable $A_1$ adenosine receptor agonist, including but not limited to adenosine; cyclohexyladenosine; various N6-substituted $A_1$ adenosine agonists including but not limited to $N^6$ cyclopentyladenosine, $N^6$ R-phenylisopropyladenosine, 2-chloro $N^6$ cyclopentyl adenosine (CCPA), $N^6$ (p-sulfophenyl) alkyl and $N^6$ sulfoalkyl derivatives of adenosine (such as $N^6$-(p-sulfophenyl) adenosine; 1-deaza analogues of adenosine including but not limited to $N^6$ cyclopentyl 1-2-chloro-1-deaza adenosine (1-deaza-2-Cl-CPA); $N^6$ cycloaklyladenosines; $N^6$ bicycloalkyladenosines; ribose modified adenosine receptor analogues including but not limited to 3'-deoxy-R-PIA. See, e.g., Conti, *Naunyn-Schmiedeberg's Arch. Pharmacol.* 348:108 (1993); Trivedi, *J. Med. Chem.* 32:8 (1989); Jacobsen, *J. Med. Chem.* 35:4143 (1992); Thedford, *Expl. Cell. Biol.* 57:53 (1989); Trewyn, *Exp. Pharmacol.* 28:607 (1979); Fleysher, *J. Amer. Chem. Soc.* (August 1968); Fleysher, *J. Amer. Chem. Soc.* (November 1969)); cycloalkyladenosines (see e.g., Moos, *J. Med. Chem.* 28:1383 (1985)); analogs of R-PIA, CHA, and CPA (see, e.g., Cristalli, *J. Med. Chem.* 31:1179 (1988)). Van der Wenden, *J. Med. Chem.* 38:4000 (1995); Jacobson, *PJM Med. Res. Rev.* 12:423 (1992); Daly, *J. Med. Chem.* 25:197 (1982). The binding of these $A_1$ adenosine receptor agonists to $A_1$ adenosine receptors and their activation may be enhanced by an allosteric enhancer such as P(2-amino-4,5-dimethyl 1-3-thienyl)-[3-trifluoromethyl phenyl] methadone. Additional $A_1$ adenosine receptor agonists are known in the art (see, e.g., *Abstracts from Purines'96, Drug Dev. Res.*, March 1996: Knutsen et al. (p. 111); Franchetti et al. (p. 127); Di Francesco et al. (p. 127); van der Wenden et al. (p. 128); Kirkpatrick et al. (p. 128); van Schaick et al. (p. 128)). Optimal dosing and administration schedules may be determined using routine methods known to those in the art.

In another embodiment of the present invention, the cells are first treated ("primed") to enhance $A_1$ adenosine receptor activity. Cells are primed prior to activation by $A_1$ adenosine receptor agonists. For example, macrophages may be primed using any priming agent known in the art, including but not limited to PMA (see, e.g., Leaver, *FEMS Microbiol. Immunol.* 47:293 (1989); White, *J. Biol. Chem.* 259:8605 (1984)); lipopolysaccharide (LPS) (see, e.g., Glaser, *J. Biol. Chem* 265:8659 (1990); Pace, *J. Immunol.* 126:1863 (1981); Alexander, *Nature New Biol.* 232:76 (1971)); platelet activating factor (PAF) (see, e.g., Stewart, *Immunology* 78:152 (1993); Salzer, *J. Clin. Invest.* 85:1135 (1990)); tumor necrosis factor alpha ($TNF_\alpha$) or thrombin (see, e.g., Stewart, *Immunology* 78:152 (1993)); f-met-leu-phe (FMLP) (see e.g., Stewart, *Immunology* 78:152 (1993)); zymosan (Rankin, *J. Clin. Invest.* 86:1556 (1990); macrophage stimulating factors including granulocyte macrophage colony stimulating factor (GM-CSF); ionomycin (for example in 1 $\mu$M amounts); calcium ionophore (such as A 23187, for example in 0.1–10 $\mu$M amounts); gamma interferon (IFN$\tau$, for example in 1–150 units/ml amounts) Flebbe, *J. Immunol.* 145:1505 (1990); supernatants of tumor cells (Hamilton and Adams, *Immunology Today* 8:151 (1987); Marvin, *J. Surg. Res.* 63:248 (1996)); or bacterial products from gram positive organisms (see, e.g., *Bacterial Endotoxin Linopolvsaccharides*, Morrison and Ryan (Eds.) CRC Press, Boca Raton, Fla., 1992; Hamilton and Adams, *Immunology Today* 8:151 (1987); Loppnow, *Methods Enzymol.* 236:3 (1994)). Preferred priming conditions for the type of cell to be activated may be determined using routine methods known to those in the art. For example, resident tissue macrophages may be primed with PMA in vivo, in the tumor or in tissues surrounding the tumor to be treated, then exposed to an $A_1$ adenosine receptor agonist in order to activate the macrophages.

In another embodiment of the present invention, priming of the cells to increase $A_1$ adenosine receptor activation includes subjecting the cells to hypoxia and reoxygenation, for example, by placing cells (for example, macrophages) in a cell chamber and subjecting them to low oxygen tension (e.g., 0–12% oxygen) for a suitable time (e.g., from about 5 minutes to about 48 hours, more preferably from about 2 hours to about 4 hours), prior to treatment with a priming agent as discussed above. See Lum, *Circ. Res.* 70:991 (1992); Ogawa, *Am. J. Physiol* 262:C546 (1992); Milhoan, *Am. J. Physiol.* 263:H956 (1992); Arya, *J. Surg. Res.* 59:13 (1995). Optimal hypoxia and reoxygenation conditions may be determined by routine experimentation as would be apparent to one skilled in the art. Such treatment of the cells is designed to increase $A_1$ adenosine receptor activity. Increased $A_1$ adenosine receptor activity may be due, for example, to an increase in the number of receptors, an increase in G-protein ($G_i$ protein responsible for coupling of $A_1$ adenosine receptors to signal transduction pathways), or an increase in enzymes responsible for the signal transduction processes. Priming procedures may be assessed, for example, by measuring receptor binding ($A_1$ adenosine binding with saturation experiments); a decrease in forskolin-stimulated cAMP; levels of G protein; or release of superoxide ion ($O_2$—), $TXA_2$ (thromboxane), PAF (platelet activating factor), or cytokines (IL-1 or TNF$\alpha$); and intracellular levels of enzymes responsible for cytokine release (e.g., phospholipase $A_2$). See, e.g., Stewart, *Immunology* 78:152 (1993); Salzer, *J. Clin. Invest.* 85:1135 (1990); Liang *J. Pharmacol. Exp. Ther.* 249:775 (1989). Combinations of hypoxia and priming agents may be used to prime cells for use in the present methods.

As discussed above, additional treatments of the cells to be activated may optionally include those which increase the numbers of receptors on the cell (e.g., transfection with plasmid vectors containing cDNA encoding $A_1$ adenosine receptors); treatment with dexamethasone); treatment with allosteric enhancers to increase $A_1$ adenosine receptor ligand binding and stabilize $A_1$ adenosine receptor-G protein complexes; treatment with protein kinase inhibitors to prevent tolerance to $A_1$ adenosine receptor agonists; or tyrosine phosphatase inhibitors to enhance LPS-induced TNF$\alpha$ release.

A further embodiment of the present invention includes, in addition to treating the cells with an $A_1$ adenosine receptor agonist, treating the cells with an $A_2$ adenosine receptor antagonists, including but not limited to triazoloquinazoline (CGS15943)(Williams *J. Pharmacol. Exp. Ther.* 241:415); pyrazolo[4,3-e]-1,2,4-triazolo [1,5-C] pyrimidine derivatives such as 7-2(phenylethyl)-5-amino-2-(2-furyl)-pyrazolo-[4.3-e]-1,2,4triazolo[1,5-c] pyrimidine (Baraldi, *J. Med. Chem.* 39:1164 (1996); Zocchi *J. Pharmacol. Exp. Ther.* 276:398 (1996)); 8-(3-chlorostyryl)caffeine (Mathot *J. Pharmacol. Exp. Ther.* 275:245 (1995)); 8-(3-isothiocyanatostyryl)caffeine (Ji, *Drug Dev. Res.* 29:292 (1993)); E-1,3-diakyl-7-methyl-8-(3,4,5-trimethoxy-styryl) xanthines, (E)-1,3-dipropyl-7-methyl-8-(3,4-dimethoxystyryl)xanthine (Shimada, *J. Med. Chem.* 35:2342 (1995); Jackson *J. Pharmacol. Exp. Ther.* 267:1993); 4-(2-[7-amino-2-{2-furyl} {1,2,4} triazolo{2,3-a} {1,3,5}triazin-5-yl-amino] ethyl)phenol (Palmer, *J. Pharmacol. Exp. Ther. Mol. Pharmacol.* 48:970 (1995)); 7-deaza-9phenyladenines (Daly, *Biochem. Pharmacol.* 37:3749 (1988); see also *Abstracts from Purines '96, Drug Dev. Res.*, March 1996 at p. 113 (Vittori et al.), p. 130 (Dionisotti et al.), p. 174 (Suzuki et al.), and p. 179 (Suzuki et al. and Dionisotti et al.); $A_3$ adenosine receptor antagonists (see, e.g., Jacobson, *Abstracts from Purines '96, Drug Dev. Res.*, March 1996 at p. 112). (Vittori et al.)

The methods of the present invention utilize the cytotoxic effects of activated treatment cells (including but not limited to macrophages, monocytes and splenocytes) to inhibit the growth of tumors, cancers and other neoplastic tissues. The methods of treatment disclosed herein may be employed with any subject suspected of carrying tumorous growths, cancers, or other neoplastic growths, either benign or malignant ("tumor" or "tumors" as used herein encompasses tumors, cancers, disseminated neoplastic cells and localized neoplastic growths). Examples of such growths include but are not limited to breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; kidney cancers; endocrine cancers; skin cancers; melanomas; angiomas; and brain or central nervous system (CNS) cancers. In general, the tumor or growth to be treated may be any tumor or cancer, primary or secondary, which is recognized by cytotoxic cells (for example, macrophages) and which induces the tumoricidal effect of the cells upon contact. See, e.g., Alexander and Evans, *Nature New Biology* 232:76 (1971).

The route of administration of activated cells will vary depending on the subject being treated and the neoplasm being treated. Some tumors which may be treated by the method of the present invention are cystic tumors: that is, tumors which grow around a fluid-filled cavity, or cyst. Examples of such cystic tumors include (but are not limited to) cystic glioblastomas and cystic astrocytomas. In such tumors the priming agent and the $A_1$ adenosine receptor agonist (or the activated cells) of the present methods may be administered directly into the cystic cavity.

For administration, the activated cells may be mixed, prior to administration, with a non-toxic, pharmaceutically acceptable carrier substance (e.g. normal saline or phosphate-buffered saline), and may be administered using any medically appropriate procedure as will be apparent to those of ordinary skill in the art, e.g., intravenous or intra-arterial administration, injection into the cerebrospinal fluid, intradermal administration, intraperitoneal administration, intracavity administration (e.g., via endoscopy of a body cavity, such as bronchoscopy or thoracoscopy), intrathecal administration or direct administration to the tumor or to an artery supplying the tumor, or isolated perfusion of an affected limb. In addition, either intrathecal administration or injection into the carotid artery are advantageous for therapy of tumors located in the brain. Administration may occur with surgical exposure of the tumor, or visualization techniques as are known in the art may be used to guide invasive administration. The methods of the present invention may be used in combination with other treatment modalities, such as chemotherapy or radiotherapy.

Where the tumor is a solid tumor, administration may occur by first creating a resection cavity in the location of the tumor and then depositing the activated cells in the resection cavity in like manner as with cystic tumors.

Dosage of the activated treatment cells will depend, among other things, on the type of activated cell utilized (for example, macrophages, monocytes and/or splenocytes), the subject and the tumor being treated, the route of administration, and the sensitivity of the tumor being treated.

As used herein, "treatment" of a tumor or cancerous growth refers to methods of inhibiting or slowing the growth or increase in size of a tumor or cancerous growth, reducing neoplastic cell numbers, or preventing spread to other anatomic sites, as well as reducing the size of a neoplastic growth or numbers of neoplastic cells. As used herein, "treatment" is not meant to imply cure or complete abolition of neoplastic growths.

As used herein, "contacting" a cell with a substance means (a) providing the substance to the environment of the cell (e.g., solution, in vitro culture medium, anatomic fluid or tissue) or (b) applying or providing the substance directly to the surface of the cell, in either case so that the substance comes in contact with the surface of the cell in a manner allowing for biological interactions between the cell and the substance.

The ability of activated cells to associate with tumor cells may also be utilized for methods of imaging or diagnosing tumorous or neoplastic growths. In the diagnostic or imaging methods of the present invention, radiolabelled $A_1$ adenosine receptor agonists (preferably selective for $A_1$ adenosine receptors) and/or $A_2$ adenosine receptor antagonist ligands are used to label the cells (such as macrophages). (See Palmer, *JPET Mol. Pharmacol.* 48:970, 1995 regarding $A_1$ agonists or $A_2$ antagonists.) Where the ligands are $A_1$ adenosine receptor agonists they additionally activate the cells as described above and may serve both imaging and therapeutic purposes. After administration of the radiolabelled activated cells to a subject and after a suitable time has elapsed to allow association of activated cells and tumor cells (which time will vary depending on mode of administration of the labelled macrophages and site of the tumor), detection of the labelling signal is used for imaging or diagnostic (or therapeutic) purposes as are known in the art.

As used herein, "imaging" means the treatment of tumor cells such that they can be distinguished from non-tumor cells. Imaging methods are useful in diagnosing or screening for the presence of a benign or malignant growth, assessing changes in size or extent of a growth, as well as in localizing a growth for treatment or surgical excision. The imaging methods disclosed herein may be employed to image neoplastic growths in subjects diagnosed with such conditions, as well as for screening subjects suspected of having neoplastic growths, e.g., both subjects who have been previously diagnosed with a neoplastic condition, and subjects who have not been previously diagnosed with a neoplastic condition. Subjects are typically humans, but also include veterinary subjects, including but not limited to dogs, cats, horses, cows and other companion and livestock species.

Techniques for preparing and utilizing radioactively labeled adenosine receptor ligands are known in the art. See, e.g., Williams and Jacobson, *Radioligand Binding Assays for Adenosine Receptors*, In: Adenosine and Adenosine Receptors, M. Williams (Ed.), Humana Press, Clifton, N.J. (1990); Patel et al., *Molecular Pharmacology* 33:585 (1988); Williams et al., Receptor Pharmacology and Function, Marcel Dekker, New York (1988).

For imaging and/or diagnostic purposes, the labeled cells may be administered systemically or locally, to areas where tumor growth is suspected. Suitable routes of administration include those discussed above for therapeutic uses of activated cells.

The following examples are provided to illustrate the present invention, and should not be construed as limiting thereof.

EXAMPLE 1

Isolation of Monocytes

Monocytes are isolated from peripheral blood of human or animals subjects using techniques known in the art. In human subjects, peripheral blood mononuclear cells may be obtained by plataletpheresis and purified on ficoll-percoll (Prabhakar et al., *Int. J. Immunopharmac.* 17:221–224 (1995); Prabhakar et al., *Int. J. Immunopharmac.* 15:205–209 (1993)). Monocytes may alternatively be isolated using counterflow elutriation. Bohnsack et al. *J. Immunol.* 136:3793 (1986).

The above techniques provide a sample of isolated peripheral monocytes.

EXAMPLE 2

Differentiation of Monocytes In Vitro

Monocytes isolated as described in Example 1 are cultured in viltro. Suitable culture media include RPMI-1640 supplemented with FCS (Prabhakar et al., *Int. J. Immunopharmac.* 17:221–224 (1995); Bohnsack et al. *J. Immunol.* 136:3793 (1986)) 1–20% serum. In vitro differentiation of peripheral monocytes to macrophages is known in the art. Eppell, *J. Immunol.* 143:4141 (1989). In vitro culture for 5–6 days increases adenosine binding to the cultured cells as evidenced by an increase in density of $A_1$ adenosine receptors ($\beta$ max) as demonstrated in saturation radioligand binding experiments with $^3$H DPCPX or $^3$H CCPA.

An in vitro culture of macrophages is provided by the above techniques. Alternatively, macrophages may be obtained from established cell lines or from depositories such as the American Type Culture Collection.

EXAMPLE 3

Priming of Human Macrophages

Isolated monocytes are cultured for 5–6 days as described in Example 2, above, to allow monocytes to differentiate into macrophages. The macrophages are then primed in vitro in the presence of 1–20% serum (normal human serum) with a known priming factor, such as effective amounts of phorbol myristoyl acetate. Amounts of PMA, and the exposure time required to prime macrophages will be apparent to those skilled in the art, and can be assessed, for example, by superoxide anion assays (Stewart, *Immunology* 78:152 (1993); Hamilton and Adams, *Immunology Today* 8:151 (1987)). Doses of other priming agents may be used, such as LPS (0.01 pg–100 ng/ml) (Glasner, *J. Biol. Chem.* 265:8659 (1990); IFNτ (1–150 μ/ml) (Flebbe *J. Immunol.* 145:1505 (1990)); FMLP; calcium ionophore or GM-CSF. Use of 0.01–1.0 μM PMA as a priming amount is reported by Yang, *Inflammation* 18:221 (1994)). See also Leaver, *FEMS Microbiology Immunol.* 47:293 (1989); Saijadi, *J. Immunol* 156:3435 (1996).

To discern the priming of macrophages, the oxidative burst may be measured by any of various methods known in the art. See, e.g., Hamilton, *Immunology Today* 8:151 (1987); Glaser et al., *J. Biol. Chem.* 265:8658 (1990).

The above techniques provide an in vitro culture of primed macrophages.

EXAMPLE 4

$A_1$ Adenosine Receptor Agonist Activation of Macrophages

To primed, cultured human macrophages provided as in Example 3, in the presence of $Mg^{2+}$ or $Ca^{2+}$ (1–100 mM) and adenosine deaminase (0.1–5 units/ml) and 1–20% serum, a selective $A_1$ adenosine receptor agonist is added to activate the macrophages to a cytotoxic state. Suitable selective $A_1$ agonists and conditions are well known in the art and include for example, R-phenylisopropyladenosine (R-PIA, 0.1–100 μM; see Tey et al., *Biochem. Biophys. Res. Comm.* 187:1486 (1992)); S-ENBA; CPA ($10^{-10}$–$10^{-8}$ M; Priebe Cancer Res. 50:4328 (1990)) or $CCPA_1$ added for a time period of 1–6 hours (Pace *J. Immunol.* 126:1863 (1981)) to activate the cultured macrophages.

To a duplicate sample of primed, cultured human macrophages treated as above, an $A_2$ adenosine receptor antagonist such as DMPX (20μm) (Prabhakar, *Int. J. Immunopharm.* 17:221 (1995)) or CSC (Mathot et al., *J. Pharm. and Exp. Ther.* 275:245 (1995); SCH58261 (1–300 nM) (Zocchi, *J. Pharmacol. Exp. Ther.* 276:398 (1996)) is also added for up to 5 hours. This sample is utilized to determine the effect of $A_2$ adenosine receptor agonist on LPS-induced TNFα release, and to show that in the presence of the $A_2$ antagonist an $A_2$ agonist is unable to prevent or inhibit LPS-induced TNFα release. Prabhakar and Brooks et al., *Int. J. Immunopharmacol.* 17:221 (1995).

EXAMPLE 5

Tumoricidal Effect of Primed, Activated Macrophages

The tumoricidal effects of primed and activated macrophages, provided by the above Examples, are demonstrated as follows. Primed, activated macrophages are placed into the wells of microtiter plates containing culture media. Suitable microtiter plates are readily commercially available.

Cells of any suitable human tumor cell line, as are readily available commercially, are prelabelled with [51] Cr (see, e.g., Pace, *J. Immunol.* 126:1863 (1981) at p. 1864) and are seeded into multiple wells at a concentration of macrophages:tumor cells 12.5–100:1 (Pace, *J. Immunol.* 126:1863 (1981); Sato *Int. J. Cancer* 66:98 (1996)). Control wells containing only radiolabelled tumor cells or only treated macrophages are also provided. Over an extended period (from about four, up to about 16 hours, about 24 hours, or more than 24 hours, see Alexander, *Nature New Biology* 232:76 (1971) and Sato, *Int. J. Cancer* 66:98 (1996)) the uppermost 0.1 μl of supernatant is removed from one or several wells and assayed for radioactivity using techniques known in the art. See, e.g., Pace, *J. Immunol.* 126:1863 (1981); Sato, *Int. J. Cancer* 66:98 (1996); or Flebbe, *J. Immunol.* 145:1505 (1990). The measurement of radioisotope release from tumor cells provides a measure of cell death and is compared to controls. The release of radioisotope over time is charted to indicate cytotoxic effects over time.

EXAMPLE 6

Release of Cytotoxic Factors by Primed, Activated Macrophages

Multiwell plates containing primed, activated macrophages as described in Example 4, above, are prepared. Over an extended period (up to 24 hours or more), samples are removed from one or several wells and assayed for the presence of cytotoxic factors, including but not limited to Tumor Necrosis Factor alpha (TNFα) thromboxane ($TXA_2$) [$TXB_2$ (stable metabolite of thromboxane)], and Interleukin-1 as are known in the art. ELISAS or radioimmunoassays to detect the presence of these factors are commercially available, or would be apparent to one skilled in the art. The release of cytotoxic factors over time is charted to indicate cytotoxic effects of the macrophages over time.

The foregoing is illustrative of the present invention and is not to be construed as limiting thereof. The invention is defined by the following claims, with equivalents of the claims to be included therein.

That which is claimed is:

1. A method of imaging tumor cells in vivo in a subject, comprising:
   (a) obtaining a sample of treatment cells from a subject, said treatment cells selected from the group consisting of macrophages, monocytes and splenocytes;
   (b) priming said treatment cells by contact with a priming agent in an amount sufficient to prime said treatment cells;
   (c) labeling said treatment cells with a radiolabelled A1 adenosine receptor agonist, said A1 adenosine receptor agonist provided in an amount sufficient and for a time sufficient to induce cytotoxicity in said treatment cells; and then
   (d) administering said labelled treatment cells to the subject in an amount effective to provide a radioimage of tumor cells present in said subject.

2. The method of claim 1 wherein said selective $A_1$ adenosine receptor ligand is a selective $A_1$ adenosine receptor agonist in an amount sufficient to induce cytotoxicity in said treatment cells.

3. The method of claim 1 wherein said treatment cells are monocytes, and said monocytes are cultured to provide macrophages for priming in step (b).

4. The method of claim 1 wherein said priming agent is selected from the group consisting of phorbol myristoyl acetate (PMA), lipopolysaccharide (LPS), interferon gamma (IFNτ), granulocyte-macrophage colony stimulating factor (GMCSF), and f-met-leu-phe (FMLP).

5. The method of claim 1 wherein said subject is human.

6. The method of claim 1 further comprising contacting said treatment cells to an allosteric enhancer in an amount effective to enhance the binding of $A_1$ adenosine receptor agonists to $A_1$ adenosine receptors.

7. The method of claim 1 further comprising contacting said treatment cells to dexamethasone in an amount effective to increase the number of $A_1$ adenosine receptor receptors on said treatment cells.

8. The method of claim 1 further comprising contacting said treatment cells to a protein kinase inhibitor.

9. The method of claim 1 further comprising the step of contacting said treatment cells to an $A_2$ adenosine receptor antagonist.

10. The method of claim 1 further comprising, prior to step (b), subjecting said treatment cells to a period of hypoxia and re-oxygenation sufficient to increase $A_1$ adenosine receptor activity.

11. The method of claim 1 wherein said administering step is carried out by administering said labelled treatment cells systemically to the subject.

12. The method of claim 1 wherein said administering step is carried out by administering said labelled treatment cells directly to tissue suspected of containing tumor cells.

* * * * *